US008058436B2

(12) United States Patent
Wieringa et al.

(10) Patent No.: US 8,058,436 B2
(45) Date of Patent: Nov. 15, 2011

(54) METHOD FOR THE PREPARATION OF ENANTIOMERICALLY PURE MIRTAZAPINE

(75) Inventors: Johannes Hubertus Wieringa, Oss (NL); Adrianus Antonius Martinus Van De Ven, Oss (NL); Gerardus Johannes Kemperman, Oss (NL)

(73) Assignee: N.V. Organon, Oss (NL)

( * ) Notice: Subject to any disclaimer, the term of this patent is extended or adjusted under 35 U.S.C. 154(b) by 221 days.

(21) Appl. No.: 10/564,193

(22) PCT Filed: Jul. 5, 2004

(86) PCT No.: PCT/EP2004/051357
§ 371 (c)(1),
(2), (4) Date: Jan. 6, 2006

(87) PCT Pub. No.: WO2005/005410
PCT Pub. Date: Jan. 20, 2005

(65) Prior Publication Data
US 2006/0229300 A1    Oct. 12, 2006

(30) Foreign Application Priority Data

Jul. 10, 2003  (EP) .................................. 03102095

(51) Int. Cl.
*C07D 241/36* (2006.01)
(52) U.S. Cl. ...................................................... 544/343
(58) Field of Classification Search .................. None
See application file for complete search history.

(56) References Cited

U.S. PATENT DOCUMENTS

| 4,062,848 | A | 12/1977 | van der Burg | 260/268 PC |
| 6,376,668 | B1 | 4/2002 | Iishi et al. | 544/360 |

FOREIGN PATENT DOCUMENTS

| WO | WO 99/25356 | 5/1999 |
| WO | WO 00/62782 A1 | 10/2000 |
| WO | WO 01/23345 | 4/2001 |
| WO | WO 01/58453 | 8/2001 |

OTHER PUBLICATIONS

March Advanced Organic Chemistry, 1992, pp. 250-252.*
"Dissociation constants of organic acids and bases", http://www.zirchrom.com/organic.htm, accessed Mar. 17, 2008.*
Pizey. Synthetic Reagents, vol. 6, 1985, pp. 270-275 and 372-414.*

International Search Report No. PCT/EP2004/051357 dated Dec. 1, 2004.
Selditz, U. et al., "Direct enantiomeric separation of mianserin and 6-azamianserin derivatives using chiral stationary phases," Journal of Chromatography A., vol. 803, No. 1-2 (1998) pp. 169-177.
O'Connor, W. T. et al., "Effect of Chronic Administration of the 6-AZA Analogue of Mianserin (Org. 3770) and its Enantiomers on Behaviour and Changes in Noradrenaline Metabolism of Olfactory-Bulbectomized Rats in the 'Open Field' Apparatus," Neuropharmacology, vol. 25, No. 3 (1986) pp. 267-270.
Kooyman, A. R. et al., "Interaction between Enantiomers of Mianserin and ORG3770 AT 5-HT$_3$ Receptors in Cultured Mouse Neuroblastoma Cells," Neuropharmacology, vol. 33, No. 33/4 (1994) pp. 501-507.
De Boer, Th., et al., "Neurochemical and Autonomic Pharmacological Profiles of the 6-AZA-Analogue of Mianserin, Org 3770 and its Enantiomers," Neuropharmacology, vol. 27, No. 4 (1988) pp. 399-408.
Gower, A. J. et al., "Pharmacological Evaluation of in Vivo Tests for $\alpha_2$-Adrenoceptor Blockade in the Central Nervous System and the Effects of the Enantiomers of Mianserin and its Aza-analog ORG 3770," vol. 291, (1988) pp. 185-201.
Collins, A. N. et al., "Methods for Obtaining Optically Active Compounds," Chirality in Industry, John Wiley (1992) 16 pages.
Written Opinion for International Application No. PCT/ep2004/051357 mailed Dec. 1, 2004.

* cited by examiner

*Primary Examiner* — Noble Jarrell
(74) *Attorney, Agent, or Firm* — Susan L. Hess; Gerard M. Devlin

(57) ABSTRACT

The invention provides a method for the preparation of enantiomerically pure mirtazapine, said method comprising a step of ring closure of a compound of formula (II) wherein X is a leaving group, said step comprising treatment with an acid, whereby mirlazapine with enantiomeric excess is formed by the ring closure of the compound of formula (II) with enantiomeric excess by treatment with a suitable acid in the absence of a solvent or a suitable combination of an acid and an organic solvent.

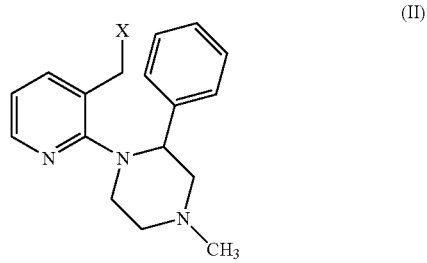

(II)

3 Claims, No Drawings

METHOD FOR THE PREPARATION OF ENANTIOMERICALLY PURE MIRTAZAPINE

This application claims priority based on International Patent Application No. PCT/EP2004/051357, filed Jul. 5, 2004, and European Application No. 03102095.1, filed Jul. 10, 2003.

The present invention relates to a method for the preparation of enantiomerically pure mirtazapine comprising ring closure with an add.

Mirtazapine, 1,2,3,4,10,14b-hexahydro-2-methyl-pyrazino[2,1-a]pyrido[2,3-c][2]benzazepine is a tetracyclic compound having the formula I:

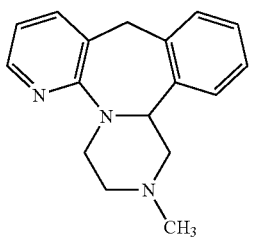

The compound is chiral and the racemic mixture finds widespread use as a medicine for the treatment of depression. Other medical uses for mirtazapine have also been reported e.g., WO 99/25356 and WO 01/58453 disclose its use in the treatment of sleep disorders and apnea. Investigations into the biological effects of the enantiomers of mirtazapine (e.g. O'Connor and Leonard, Neuropharmacology, 1986, vol. 25, pp. 267-270; Kooyman et al., 1994, vol. 33, pp. 501-507; De Boer et al., Neuropharmacology, 1988, vol. 27, pp. 399-408; Gower et al., 1988, vol. 291, pp 185-201) invoke the use of the compound in its pure enantiomeric forms, which opens the need for efficient production of large quantities of enantiomerically pure mirtazapine. The present invention provides for improvement in such a production method.

A variety of methods are known in the art for the preparation of mirtazapine. U.S. Pat. No. 4,062,848 describes variations within a four stage synthetic scheme by which the synthesis of mirtazapine can be accomplished starting from a 2-substituted nicotinitrile. Further modifications to various stages of this route have subsequently been described in WO 00/62782, WO 01/23345 and U.S. Pat. No. 6,376,668.

The preparation of enantiomerically pure mirtazapine has been addressed in U.S. Pat. No. 4,062,848, WO 00162782 and Selditz et al., 1998 (J. Chromatography, 1998, vol 803, pp 169-177). By the method disclosed in U.S. Pat. No. 4,062,848, enantiomerically pure mirtazapine is obtained by fractional crystallisation of the diastereoIsomeric salts formed by reaction of racemic mirtazapine with enantiomerically pure dibenzoyltartaric acid in ethanol followed by regeneration of the free base by treatment with aqueous ammonia. Other methods of forming pure mirtazapine by recrystallisation of crude mirtatapine are disclosed in WO 00/62782. Selditz et al. describe a chromatographic method to separate the enantiomers. In these methods resolution occurs at the end of the synthetic pathway leading to the generation of a racemic mixture of mirtazapine. It follows therefore that the overall yield of each enantiomerically pure compound obtained is relatively low and can never be more than 50%. It would be beneficial to have a more economic method in which enantiomerically pure mirtazapine could be prepared with an overall improved yield.

According to the method described in U.S. Pat. No. 4,062,848 mirtazapine can be obtained as a result of ring closure of a compound of formula (II),

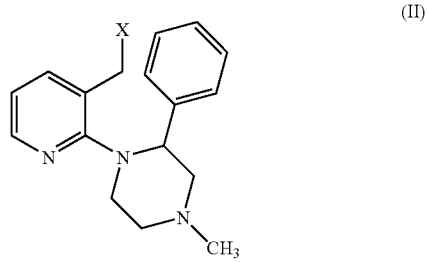

wherein X can represent a leaving group, such as a hydroxyl group, an esterified or etherified hydroxyl group or a halogen, using a variety of ring dosing reagents. Examples of such reagents include acids such as sulfuric acid, concentrated hydrochloric acid, picric acid, trifluoroacetic acid, phosphoric acid, polyphosphoric acid (PPA), phosphorus oxychloride, phosphorus trioxide, phosphorus pentoxide and Lewis Acids such as aluminium chloride, ferric chloride, zinc chloride, tin chloride, titanium chloride, boron trifluoride, antimony pentachloride and zirconium tetrachloride. In U.S. Pat. No. 4,062,848 preparation of mirtazapine is exemplified by ring closure using concentrated sulfuric acid. In WO 00/62782 it is indicated that concentrated sulfuric acid is most preferred. In U.S. Pat. No. 4,062,848 a remark is made that pure enantiomers of mirtazapine might be obtained synthetically by using enantiomerically pure starting material for the last ring closure step. However, the method described in WO 00/62782 with concentrated sulfuric acid does not sufficiently retain optical purity. Apparently, those reaction conditions allow excessive racemisation.

Surprisingly, it has now been found that for the synthesis of enantiomerically pure mirtazapine by ring closure of an enantiomerically pure compound of formula (II), stereochemical integrity in the starting material can nevertheless be preserved by making a specific selection out of the above mentioned ring closing reagents.

The present invention therefore provides a method comprising a step of ring closure of a compound according to formula (II), wherein X is a leaving group, said step comprising treatment, wherein mirtazapine with enantiomeric excess is formed by the ring closure of the compound of formula (II) with enantiomeric excess by treatment with a suitable acid in the absence of a solvent or a suitable combination of an acid and an organic solvent. The alcohol according to formula II is preferably used as crystalline salt or solvate, such as the oxalate salt of (S) or (R) 1-(3-hydroxymethyl-2-pyridyl)-4-methyl-2-phenylpiperazine. Optionally, dicalite is added to the reaction mixture to prevent lump formation.

The term mirtazapine is used here in its generic meaning commonly used to refer to the chemical compound as a base and, depending on the context, to the salts and solvates thereof and supplemented with the prefixes (R) or (S) and/or (+) or (−) to the enantiomers of the compound. The (S) configuration causes positive optical rotation in the usual solvents.

The term enantiomeric excess in a compound refers to the difference between the amounts of each of the enantiomers present in a mixture, relative to the total amount of the compound in the mixture expressed as percentage. For example, in a 10 g mixture containing 9 g mirtazapine (90%), of which 4 g is (R)mirtazapine and 5 g is (S)-mirtazapine the enantiomeric excess of the (S)-enantiomer is about 11%. In an abbreviated manner the term mirtazapine or compound with enantiomeric excess refers to a mixture containing the mirtazapine or the compound with enantiomeric excess.

The invention can provide enantiomerically pure mirtazapine if enantiomerically pure starting material is used and the ring closure is effected by treatment with a suitable acid in the absence of a solvent or a suitable combination of an acid and an organic solvent.

Enantiomerically pure compound is one comprising less than 20% of the other enantiomer, which is an enantiomeric excess of 60%. Depending on the specific conditions of the invented method an enantiomerically pure compound having less than 10% of the other enantiomer or less than 1% of the other enantiomer can also be obtained. The yields of enantiomerically pure mirtazapine isolated are typically not less than 50% but yields of not less than 70% can also be obtained.

A leaving group is a reactive function on a molecule which undergoes displacement from the molecule when a new bond is formed, as is commonly known in the art. More specifically a leaving group can be a hydroxyl group, an activated ester thereof, such as a carboxylate, a sulfonate or a phosphonate, or a halogen. Groups with this function are commonly known in the art and the list can be further expanded by consultation of commonly available handbooks for organic synthesis.

A suitable acid for the method of the present invention is defined to be a specific acid or acid/solvent combination as mentioned hereafter or an acid or acid/solvent combination not mentioned hereafter, but which is obtained by performing a test as to the suitability of the acid. The test is to perform the ring closure with an acid, being a candidate acid, and starting material, which is compound II as defined above, or a salt or solvate thereof, in a predetermined enantiomeric purity, and determine after the reaction the enantiomeric excess of the resulting mirtazapine. The quantitative degree of loss of enantiomeric purity can be determined by simple calculation and expressed as difference between enantiomeric excess in the starting material before the reaction and the enantiomeric excess of the product mirtazapine after the reaction. If the loss is less than 40% the acid or acid/solvent combination is a suitable acid or acid/solvent combination. A more strict criterion for a suitable acid or acid/solvent combination can be applied by selecting those causing a loss less than a number anywhere between 0% and 40%, such as 35%, 30%, 25%, 20%, 15%, 10%, 5%, 2%, 1%, 0.5% and 0.3%. It is therefore an aspect of the invention to provide a method for the selection of an acid or acid/solvent combination suitable for the stereospecific ring closure leading to enantiomerically pure mirtazapine. The method comprises performing the ring closure reaction of an enantiomerically pure compound according to the formula II, or a salt or solvate thereof, with the meaning of X, as defined previously with any candidate acid or any candidate acid/solvent combination and determining a loss of enantiomeric excess by the reaction and identifying an acid or an acid/solvent combination, as suitable if it results in the loss of less than 40%. Optionally, a stricter criterion, as mentioned above can be applied for more suitable acids or acid/solvent combinations.

A suitable acid used in the absence of solvent can be a protic acid or a protic acid derivative such as a protic acid anhydride. Concentrated sulfuric acid, the prior art method of choice for the preparation of racemic mirtazapine, or aluminium trichloride is not suitable.

For ring closure using a suitable acid in the absence of solvent, the use of polyphosphoric acid or phosphorus pentoxide in phosphoric acid are particularly preferred. It is recommended to use polyphosphoric acid, or phosphorus pentoxide in phosphoric acid, in an amount of low excess over the starting alcohol defined as compound 11 above. The reaction will give better yield and better retention of enantiomeric excess if the ratio (w/w) of polyphosphoric acid over the alcohol (weight of base of compound II) is less than 10 to 1 (w/w), or better 5 to 1, even better if less than 2.5 to 1. When polyphosphoric acid is introduced in amounts of pentoxide and phosphoric acid (possibly in weight (w/w) ratio of pentoxide over phosphoric acid of 1:1 to 1:9) the weights of phosphorus pentoxide and phosphoric acid are added up to express as the total amount of polyphosphoric acid.

A suitable acid and organic solvent combination can be a combination of a protic acid or a protic acid derivative such as a protic acid anhydride or a mineral acid and a polar coordinating solvent such as ethanol or higher alcohols, DMF, DMA or N-methylpyrrolidinone. More preferred is to use the combination of a protic acid derivative and N-methylpyrrolidinone or DMF. Polyphosphoric acid and N-methylpyrrolidinone or DMF are particularly preferred.

The acid/solvent combinations phosphorus pentoxide or polyphosphoric acid or sulfuric acid and xylene; phosphorus pentoxide or polyphosphoric acid and chlorobenzene; phosphorus pentoxide or polyphosphoric acid and toluene, and sulfuric acid and dichloromethane are not suitable.

Whilst the ring closure reaction can take place at room temperature, the reaction can also be facilitated with additional heating. It is a further aspect of the invention therefore to include ring closure according to the methods of the present invention including additional heating.

A compound of formula (II) can be prepared by the synthetic route shown in Scheme I which is described in U.S. Pat. No. 4,062,848.

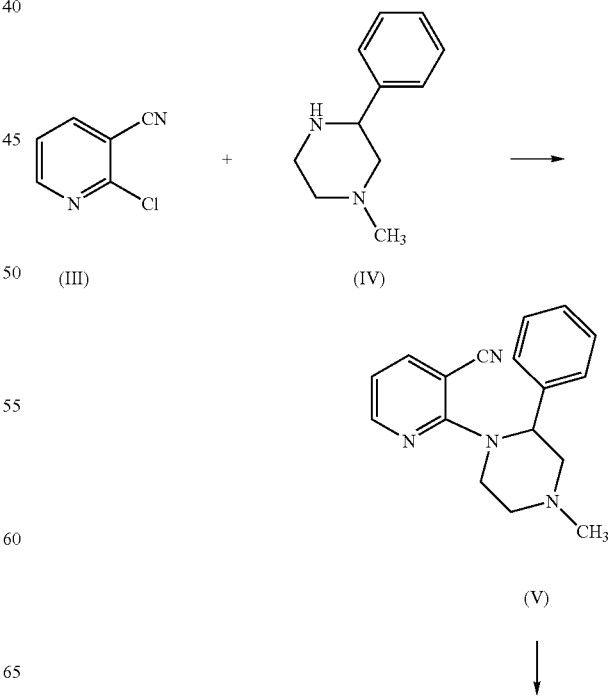

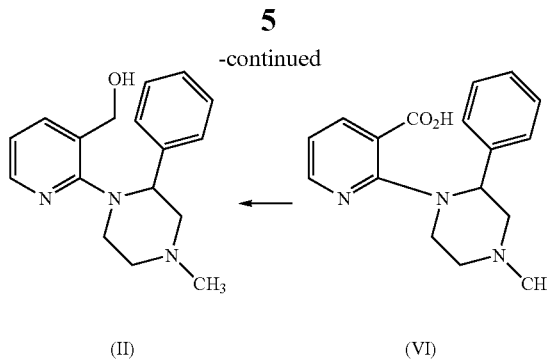

Thus, compound (V) can be prepared by reaction of compound (IV) with chloronicotinitrile (III) in an organic solvent, such as tetrahydrofuran or dimethylformamide and in the presence of an equivalent of a base such as potassium fluoride. Compound (VI) can then be prepared by hydrolysis of compound () using an aqueous base such as potassium hydroxide in an alcohol such as ethanol, typically at reflux. In WO 00/62782, it is described that the molar ratio of the base used to effectuate the nitrile hydrolysis can be reduced from 25 moles of base (as disclosed in the procedure of U.S. Pat. No. 4,062,848) to around 12 moles of base. Finally compound (II) can be prepared by reduction of compound (VI) again using a metal hydride such as lithium aluminium hydride in an organic solvent such as tetrahydrofuran. Conversion of the alcohol function to other leaving groups such as carboxylate and sulphonate esters and to halogens can be readily achieved by methods which are well known in the art.

Preparation of enantiomerically pure compound (II) can then be achieved by using methods well known in the art. For example, asymmetric synthesis methods e.g., synthesis with chiral induction, fractional crystallisation of diastereoisomeric salts formed upon reaction with a chiral acid or separation by chromatography on a chiral medium by normal or reverse phase chromatographic methods. Such methods are for example described in 'Chirality in Industry' (edited by A. N. Collins, G. N. Sheldrake and J. Crosby, 1992; John Wiley)

The invention also includes enantiomerically pure mirtazapine produced by the method of the present invention and pharmaceutical compositions of such for use in therapy. Such compositions can comprise a therapeutically effective amount of enantiomerically pure mirtazapine in combination with pharmaceutically acceptable carriers and excipients which are well known in the art.

The invention is illustrated by the following examples:

EXAMPLE 1a

Preparation of [S]-mirtazapine (S)-1-(3-Hydroxymethyl-2-pyridyl)-4-methyl-2-phenylpiperazine (0.23 g, 1.03 mmol) was dissolved in N-methylpyrrolidinone (10 mL). The resulting solution was added dropwise to polyphosphoric acid (1.46 g) in N-methylpyrrolidone (5 mL) with stirring at 81° C. The reaction mixture was stirred at 100° C. for 72 h. It was then diluted with sodium hydroxide solution and diethyl ether. The organic layer was separated and washed twice with water. Magnesium sulfate was added, removed by filtration and the filtrate was evaporated. The title compound (0.19 g, 68%) was obtained as an oily product. The enantiomeric excess (e.e.) of the product was 99.2%.

EXAMPLE 1b

To a mixture of polyphosphoric acid (41.8 g) and N-methylpyrolidine (10.5 ml) was added a solution of (S)-1-(3-Hydroxymethyl-2-pyridyl)-4-methyl-2-phenylpiperazine (7.02 g, 24.7 mmol) in N-methylpyrrolidinone (10 mL). The reaction mixture was heated to 130° C. for 1 hour. To the reaction mixture were added water (152 ml), dicalite (8.8 g), toluene (76 ml), and 33% sodium hydroxide solution (128 ml). The aqueous layer was separated and extracted twice with toluene (76 ml). The combined toluene layers were washed three times with water (76 ml), dried with $MgSO_4$ and evaporated. This gave 4.63 g of (S)-Mirtazapine (70%) with an e.e. of 99%.

EXAMPLE 2

Preparation of (S)-mirtazapine (S)-1-(3-Hydroxymethyl-2-pyridyl)-4-methyl-2-phenylpiperazine (0.30 g, 1.0587 mmole) was dissolved in 18.75 ml of dimethylformamide. To the solution 0.75 g dicalite and 1.5 g polyphosphoric acid was added. The reaction mixture was stirred for one day at 100° C. It was then diluted with sodium hydroxide and extracted with diethyl ether. The organic layer was washed twice with water, dried with magnesium sulfate, filtered and the filtrate was evaporated. The title compound (0.19 g, 68%) was obtained as an oily product. The e.e. of the product was 99.2%.

EXAMPLE 3

Preparation of (S)-mirtazapine (S)-1(3-Hydroxymethyl-2-pyridyl)-4-methyl-2-phenylpiperazine (0.50 g, 1.76 mmole) was dissolved in N-methylpyrolidone (7.5 ml) and heated to 100° C. To this mixture dicalite (0.62 g) and phosphorus pentoxide (1.26 g) were added. After 66 hours the reaction was complete. Water was added to the reaction mixture. It was then filtered. The pH was adjusted to 14 by adding 4N sodium hydroxide solution. The aqueous solution was extracted with diethyl ether. The organic layer was dried with magnesium sulfate and evaporated. This provided the title compound (0.24 g, 51%) with an e.e. of 99.7%.

EXAMPLE 4

Preparation of (S)-mirtazapine

To [S]-1-(3-Hydroxymethyl-2-pyridyl)-4-methyl-2-phenylpiperazine (0.5 g, 1.77 mmole) was added polyphosphoric acid (9.6 g). The reaction mixture was heated to 100° C. for 20 hours. The reaction mixture was diluted with water (6.5 ml) and the pH was brought to 8 by adding 4N sodium hydroxide solution. The water layer was extracted with ethyl acetate. The organic layer was washed with water, dried with magnesium sulfate and evaporated. This provided the title compound (0.29 g, 62%) with e.e. of 76%.

EXAMPLE 5

To [S]-1-(3-Hydroxymethyl-2-pyridyl)-4-methyl-2-phenylpiperazine (1.0 g, 3.53 mmole) was added polyphosphoric acid (2 g). The reaction mixture was heated to 130° C. for 18 hours. The reaction mixture was diluted with water (6.5 ml) and the pH was brought to 8 by adding 4N sodium hydroxide solution. The water layer was extracted with ethyl acetate. The organic layer was washed with water, dried with magnesium sulfate and evaporated. This provided the title compound (0.71 g, 76%) with e.e. of 98%.

EXAMPLE 6

A solution of [S]-1-(3-Hydroxymethyl-2-pyridyl)-4-methyl-2-phenylpiperazine (1.0 g, 3.53 mmole) in dichloromethane was added to polyphosphoric acid prepared from 85% phosphoric acid (2.8 g) and phosphorouspentoxide (1.3 g). The reaction mixture was heated to 130° C. for 18 hours. The reaction mixture was diluted with water (6.5 ml) and the pH was brought to 8 by adding 4N sodium hydroxide solution. The water layer was extracted with ethyl acetate. The organic layer was washed with water, dried with magnesium sulfate and evaporated. This provided the title compound (0.79 g, 84%) with e.e. of 83%.

EXAMPLE 7

To polyphosphoric acid (20 gram) was added (S)-1-(3-hydroxymethyl-2-pyridyl)-4-methyl-2-phenylpiperazine oxalic acid salt (13.2 g, 35.3 mmole). The reaction mixture was stirred at 130° C. for 18 hours. To the reaction mixture were added water (220 ml), ethyl acetate (220 ml), and 33% sodium hydroxide solution (65 ml). The aqueous layer was separated and extracted twice with ethyl acetate (220 ml). The combined organic fractions were washed three times with water (220 ml) and evaporated. This gave 7.9 g of (S)-Mirtazapine (84%) with an e.e. of 99.2%.

EXAMPLE 8

To polyphosphoric acid (4 gram) was added (S)-1-(3-hydroxymethyl-2-pyridyl)-4-methyl-2-phenylpiperazine oxalic acid salt (1.32 g, 3.53 mmole). The reaction mixture was stirred at 130° C. for 18 hours. To the reaction mixture were added water (22 ml), ethyl acetate (22 ml), and 33% sodium hydroxide solution (6.5 ml). The aqeous layer was separated and extracted twice with ethyl acetate (22 ml). The combined organic fractions were washed three times with water (22 ml), dried with MgSO$_4$ and evaporated. This gave 0.79 g of (S)-Mirtazapine (84%) with an e.e. of 83%.

EXAMPLE 9

Preparation of (S)-mirtazapine
To sulfuric acid (30.36 ml) at a temperature of 48° C. was added a solution of (S)-1-(3-hydroxymethyl-2-pyridyl)-4-methyl-2-phenylpiperazine (15.18 g, 51.05 mmole) in ethanol (30 ml). After 1 night an additional amount of sulfuric acid (30 ml) was added. After 4 hours the reaction was complete. Water (195 ml) was added followed by a sodium hydroxide solution (8.3 M) until a precipitate formed. The aqeous layer was extracted with ethyl acetate. The organic layer was subsequently washed with sodium hydroxide solution, then sodium chloride solution, dried with magnesium sulfate and evaporated. This yielded the title compound (7.97 g, 59%) with an e.e. of 62%.

EXAMPLE 10

Provided for comparative purpose with non-suitable acid/solvent combination)

Preparation of (S)-mirtazapine
Concentrated sulfuric acid (2.2 ml) was added to (S)-1-(3-hydroxymethyl-2-pyridyl)-4-methyl-2-phenylpiperazine (029 g, 1.03 mmole). Dichloromethane was added to form a clear solution. The dichloromethane was evaporated under reduced pressure at 40° C. The reaction mixture was stirred at 48° C. After 4 hours the reaction was complete. Sodium hydroxide solution (4 N) was added until an emulsion formed. The aqueous layer was extracted with diethyl ether. The diethyl ether was washed with water, dried with magnesium sulfate and evaporated. This gave the title compound (0.17 g, 62%) with an e.e. of 36%.

The invention claimed is:
1. A method for the preparation of an enantiomer of mirtazapine comprising less than 10% of the other enantiomer, the method comprising a ring closure reaction of a compound of formula (II)

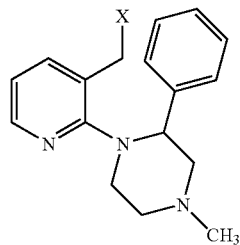

(II)

wherein X is a leaving group, the reaction comprising treatment with an acid, wherein the mirtazapine with enantiomeric excess is formed by the ring closure reaction of an R- or S-enantiomer of the compound of formula (II) by treatment with an acid or acid/solvent combination selected from the group consisting of
a) polyphosphoric acid in the absence of a solvent and wherein the weight ratio between polyphosphoric acid and the compound according to formula II is less than 2.5:1;
b) polyphosphoric acid in the presence of the solvent N-methylpyrrrolidinone or dimethylformamide; and
c) phosphorus pentoxide in the presence of the solvent N-methylpyrrolidinone and dimethylformamide.
2. The method of claim 1, wherein the enantiomer of mirtazapine is the S-enantiomer of mirtazapine.
3. The method of claim 1, wherein the acid/solvent combination is phosphorus pentoxide in the presence of N-methylpyrrolidinone.

* * * * *